(12) United States Patent
Mathur

(10) Patent No.: US 9,068,963 B2
(45) Date of Patent: Jun. 30, 2015

(54) PENTAMETHYLHEPTANE AS A PRIMARY REFERENCE STANDARD FOR CETANE NUMBER

(71) Applicant: Johann Haltermann Limited, Houston, TX (US)

(72) Inventor: Indresh Mathur, Sugar Land, TX (US)

(73) Assignee: Johann Haltermann Limited, Houston, TX (US)

(*) Notice: Subject to any disclaimer, the term of this patent is extended or adjusted under 35 U.S.C. 154(b) by 0 days.

(21) Appl. No.: 13/795,753

(22) Filed: Mar. 12, 2013

(65) Prior Publication Data

US 2014/0260510 A1    Sep. 18, 2014

(51) Int. Cl.
C10L 1/04    (2006.01)
G01N 33/28   (2006.01)

(52) U.S. Cl.
CPC .............. *G01N 33/2817* (2013.01); *C10L 1/04* (2013.01)

(58) Field of Classification Search
USPC .................................................... 585/1, 6, 14
See application file for complete search history.

(56) References Cited

U.S. PATENT DOCUMENTS

| | | | | | |
|---|---|---|---|---|---|
| 3,418,212 | A | * | 12/1968 | Fitzgibbons | 435/34 |
| 3,432,358 | A | * | 3/1969 | Cairns | 429/442 |
| 4,453,947 | A | * | 6/1984 | Shah et al. | 44/281 |
| 5,389,111 | A | | 2/1995 | Nikanjam et al. | |
| 6,311,484 | B1 | * | 11/2001 | Roth et al. | 60/301 |
| 6,949,180 | B2 | * | 9/2005 | Krug et al. | 208/15 |
| 7,118,605 | B2 | * | 10/2006 | Degen et al. | 44/413 |
| 7,816,570 | B2 | * | 10/2010 | Roberts et al. | 585/240 |
| 8,975,461 | B2 | * | 3/2015 | Peters et al. | 585/310 |
| 2004/0149627 | A1 | * | 8/2004 | Koide et al. | 208/15 |
| 2011/0192216 | A1 | | 8/2011 | Huber et al. | |
| 2011/0208408 | A1 | | 8/2011 | Haskara et al. | |

FOREIGN PATENT DOCUMENTS

| | | | |
|---|---|---|---|
| JP | 07050101 | | 5/1995 |
| JP | 07300593 | A * | 11/1995 |

OTHER PUBLICATIONS

Pitz et al., "The Impact of Alternative Fuels on Combustion Kinetics" Lawrence Livermore National Laboratory, Jul. 31, 2009.*
Farrell et al., "Development of an Experimental Database and Kinetic Models for Surrogate Diesel Fuels", SAE International, 2007.*
Lunning Prak et al., "Density, Viscosity, Speed of Sound, Bulk Modulus, Surface Tension, and Flash Point of Direct Sugar to Hydrocarbon Diesel (DSH-76) and Binary Mixtures of N-Hexadecane and 2,2,4,6,6-Pentamethylheptane", Nov. 14, 2013.*
Roquemore et al., "Cobustion Science to Reduce PM Emissions for Military Platforms", Jan. 2012, available online at <http://www.dtic.mil/cgi-bin/GetTRDoc?AD=ADA555992>.*

(Continued)

*Primary Examiner* — David A Rogers
(74) *Attorney, Agent, or Firm* — Butzel Long

(57) ABSTRACT

A composition useful as a Reference Standard for measurement of Cetane Number or for use as a standard for determining a Derived Cetane Number consists essentially of a blend of n-hexadecane and 2,2,4,6,6-pentamethylheptane. The disclosed Reference Standards can be used directly as substitutes for blends of n-hexadecane and 2,2,4,4,6,8,8-heptamethylnonane in ASTM D613-10a for determining Cetane Number, or in ASTM D6890, ASTM D7170 or ASTM D7668 to determine a Derived Cetane Number.

9 Claims, 2 Drawing Sheets

(56) References Cited

OTHER PUBLICATIONS

Mathes et al., "Binary Mixtures of Branched and Aromatic Pure Component Fuels as Surrogates for Future Diesel Fuels," SAE International Journal of Fuels Lubr, vol. 3, No. 2, pp. 794-809, Oct. 25, 2010.*

Streiff et al., "Purification, Purity, and Freezing Points of Twenty-Nine Hydrocarbons of the API-Standard and API-NBS Series", Journal of Research of the National Bureau of Standards, vol. 45, No. 2, Aug. 1950.*

Machine Translation for JP 7-50101, dated May 31, 1995, 15 pages.

Carr, Matthew A. et al., "An Experimental and Modeling-Based Study Into the Ignition Delay Characteristics of Diesel Surrogate Binary Blend Fuels," Journal of Engineering for Gas Turbines and Power, ASME, Jul. 2012, vol. 134, 072803-1 to 072803-10, 10 pages.

Caton, Patrick A., et al., "Understanding Ignition Delay Effects With Pure Component Fuels in a Single-Cylinder Diesel Engine," Journal of Engineering for Gas Turbines and Power, Mar. 2011, vol. 133, 032803-1 to 032803-11, 11 pages.

PCT Publication, PCT/US2014/021726, Form PCT/ISA/220 and PCT/ISA/237 (Jul. 2014), date of mailing: Jul. 4, 2014, 10 pages.

ASTM Designation: D6890-13b "Standard Test Method for Determination of Ignition Delay and Derived Cetane Number (DCN) of Diesel Fuel Oils by Combustion in a Constant Volume Chamber," Oct. 2013.

ASTM Designation: D7668-12 "Standard Test Method for Determination of Derived Cetane Number (DCN) of Diesel Fuel Oils—Ignition Delay and Combustion Delay Using a Constant Volume Combustion Chamber Method," Nov. 2012.

ASTM Designation: D613-10a "Standard Test Method for Cetane Number of Diesel Fuel Oil," Nov. 2010.

ASTM Designation: D7170-12a "Standard Test Method for Determination of Derived Cetane Number (DCN) of Diesel Fuel Oils—Fixed Range Injection Period, Constant Volume Combustion Chamber Method," Feb. 2013.

Webpage, KIC Chemicals, Inc, 1 page, retreived from the internet Jan. 16, 2015.

Material Safety Data Sheet, TCI America, P0047, 3 pages, Jun. 8, 2007.

General Product Information: INEOS Oligomers, "Isododecane in the production of LDPE," 2006, 6 pages, Sep. 2006.

* cited by examiner

PENTAMETHYLHEPTANE AS A PRIMARY REFERENCE STANDARD FOR CETANE NUMBER

CROSS-REFERENCE TO RELATED APPLICATIONS

Not applicable.

FIELD OF THE DISCLOSURE

Disclosed herein is a primary reference standard for determining Cetane Number of a fuel and processes for determining Cetane Number and Derived Cetane Number using the primary reference standard.

BACKGROUND OF THE DISCLOSURE

Cetane Number is a measure of the ignition performance of a diesel fuel compared to the ignition performance of reference fuels in a standardized engine test. Within the context of evaluating the Cetane Number of a fuel in accordance with ASTM D613-10a ("Standard Test Method for Cetane Number of Diesel Fuel Oil"), ignition performance refers to the ignition delay of the fuel as determined in a standard test engine under controlled conditions of fuel flow rate, injection timing and compression ratio. The Cetane Number is currently defined with respect to two primary reference fuels n-cetane and heptamethylnonane. N-cetane is assigned a Cetane Number of 100, and heptamethylnonane is assigned a Cetane Number of 15. Volumetrically proportioned mixtures are assigned a Cetane Number equal to the volume percent of n-cetane added to the volume percent of heptamethylnonane multiplied by 0.15.

The Cetane Number of a test sample is determined by comparing its combustion characteristics in a test engine with those for blends of reference fuels of known Cetane Number under standard operating conditions using a bracketing handwheel procedure which varies the compression ratio (handwheel reading) for the test sample and each of two bracketing reference fuels to obtain a specific ignition delay by interpolation of Cetane Number in terms of hand-wheel reading.

A complete description of the test apparatus, reagents, reference materials, sampling, engine and instrument settings, standard operating conditions, calibration and engine qualification, and test procedure is provided in ASTM D613-10a.

The performance of a diesel engine is greatly impacted by the combustibility of the diesel fuel (light distillates oil) used. Similar to the octane number rating that is applied to gasoline to rate its ignition stability, Cetane Number is the rating assigned to diesel fuel to rate its combustion quality. For gasoline octane number signifies its ability to resist auto-ignition (also referred to as pre-ignition, knocking, pinging, or detonation). For diesel Cetane Number is a measure of the fuel's delay of ignition time (the amount of time between the injection of fuel into the combustion chamber and the actual start of combustion of the fuel charge).

Since diesels rely on compression ignition (no spark), the fuel must be able to auto-ignite—and generally, the quicker the better. A higher Cetane Number means a shorter ignition delay time and more complete combustion of the fuel charge in the combustion chamber. This, of course, translates into a smoother running, better performing engine with more power and fewer harmful emissions.

A fuel with a low Cetane Number can cause a diesel engine to operate rough and generate higher emissions as the fuel is not burned as efficiently as it might with a higher Cetane Number fuel. Low Cetane Number fuels also make it more difficult to start the engine, while a diesel fuel with a high Cetane Number will ignite more readily, burn more completely, and deliver more power than fuels with lower numbers. In other words, Cetane Number (CN) is a measure of a fuel's ignition delay which is the time period between the start of injection and the first identifiable pressure increase due to combustion of the fuel.

Historically, accurate measurements of the Cetane Number have been difficult. It requires burning the fuel in a rare diesel engine called a Cooperative Fuel Research (CFR) engine, under standard test conditions (ASTM D613 method). The operator of the CFR engine, which was first developed in 1932, uses a hand-wheel to increase the compression ratio (and therefore the peak pressure within the cylinder) of the engine until the time between fuel injection and ignition is 2.407 ms. The resulting Cetane Number is then calculated by determining which mixture of known Cetane Number Primary Standard fuel will result in the same ignition delay.

Two Primary Reference Fuels (hydrocarbons) define the Cetane Number scale and all diesel fuel and diesel fuel components are indexed to the Primary Reference Fuels. Initially, n-hexadecane (also called n-cetane or $n\text{-}C_{16}H_{34}$), which has very good ignition quality, was assigned the Cetane Number of 100, and 1-methylnaphthalene, which has a poor ignition quality, was assigned a Cetane Number of zero.

The industry had problems in producing 1-methylnaphthalene with consistent high quality and in 1962, this low Cetane Number Reference Fuel standard was replaced with 2,2,4,4,6,8,8-heptamethylnonane (also called isocetane or HMN). This chemical had better oxidation stability and was easier to use in the CFR engine. When measured against the original 1-methylnaphthalene and n-cetane standards, 2,2,4,4,6,8,8-heptamethylnonane was assigned a Cetane Number of 15.

Thus, when a fuel has the same ignition delay period as a mixture of the two Primary Reference Fuels (n-cetane+HMN), its Cetane Number is derived from the volume percent of Cetane and HMN, as follows:

$$\text{Cetane Number} = \%\,n\text{-cetane} + 0.15(\%\,\text{HMN}) = 15 + 0.85(\%\,n\text{-cetane})$$

It has been difficult to produce pure HMN in large quantities, of the right purity, at reasonable cost. Therefore, in routine operations, the two Primary Reference Fuels (n-cetane and HMN) are replaced by two Secondary Reference Fuels: T-fuel and U-fuel. Large batches of Secondary Reference Fuel pairs are calibrated against the Primary Reference Fuels and made available to testing labs. The fuel supplier provides blend ratio instructions to achieve Cetane Numbers bounded by the values for the U and T fuels.

Each set consists of a "T Fuel" having a relatively high Cetane Number (typically 72-76) and a "U Fuel" which has a relatively low Cetane Number (typically 18-20). The Cetane Numbers assigned to each batch are based on a testing program conducted by the Diesel NEG in which blends of the T and U Fuels are engine tested against the ASTM D613-10a Primary Reference Fuels (PRF) n-cetane and 2,2,4,4,6,8,8-heptamethylnonane (HMN).

Seven Secondary Reference Fuels (T and U fuel) are engine tested (ASTM D613) by various labs as follows:

| Blend No. | % T | % U |
| --- | --- | --- |
| 1 | 20 | 80 |
| 2 | 40 | 60 |

| Blend No. | % T | % U |
|---|---|---|
| 3 | 50 | 50 |
| 4 | 60 | 40 |
| 5 | 70 | 30 |
| 6 | 80 | 20 |
| 7 | 100 | 0 |

Each blend of T and U fuels is tested by bracketing the blend against the known Cetane Number blend of Primary Reference Fuels n-cetane and HMN. A regression equation for Cetane Number as a function of % T Fuel is then developed. Typical correlations for the pairs of T and U Secondary Reference Fuel batches developed by the industry over the years are listed below:

$T\text{-}24/U\text{-}17(2007)$ Cetane Number=$0.554513(\%T)+19.50861$ $T\text{-}23/U\text{-}16(2002)$ Cetane Number=$0.568440(\%T)+19.25631$ $T\text{-}22/U\text{-}15(1997)$ Cetane Number=$0.560351(\%T)+18.72438$ $T\text{-}21/U\text{-}14(1994)$ Cetane Number=$0.554019(\%T)+18.27033$ $T\text{-}20/U\text{-}13(1990)$ Cetane Number=$0.527952(\%T)+19.92739$ These equations were then used to generate the tables of accepted reference value Cetane Numbers for various blends of T and U fuel pairs as shown, typically, in Table A.

TABLE A

CETANE NUMBER for BLENDS OF T-24 AND U-17

| % T-24 | CN |
|---|---|
| 0 | 19.5 |
| 1 | 20.1 |
| 2 | 20.6 |
| 3 | 21.2 |
| 4 | 21.7 |
| 5 | 22.3 |
| 6 | 22.8 |
| 7 | 23.4 |
| 8 | 23.9 |
| 9 | 24.5 |
| 10 | 25.1 |
| 11 | 25.6 |
| 12 | 26.2 |
| 13 | 26.7 |
| 14 | 27.3 |
| 15 | 27.8 |
| 16 | 28.4 |
| 17 | 28.9 |
| 18 | 29.5 |
| 19 | 30.0 |
| 20 | 30.6 |
| 21 | 31.2 |
| 22 | 31.7 |
| 23 | 32.3 |
| 24 | 32.8 |
| 25 | 33.4 |
| 26 | 33.9 |
| 27 | 34.5 |
| 28 | 35.0 |
| 29 | 35.6 |
| 30 | 36.1 |
| 31 | 36.7 |
| 32 | 37.3 |
| 33 | 37.8 |
| 34 | 38.4 |
| 35 | 38.9 |
| 36 | 39.5 |
| 37 | 40.0 |
| 38 | 40.6 |
| 39 | 41.1 |
| 40 | 41.7 |
| 41 | 42.2 |
| 42 | 42.8 |
| 43 | 43.4 |
| 44 | 43.9 |
| 45 | 44.5 |
| 46 | 45.0 |
| 47 | 45.6 |
| 48 | 46.1 |
| 49 | 46.7 |
| 50 | 47.2 |
| 51 | 47.8 |
| 52 | 48.3 |
| 53 | 48.9 |
| 54 | 49.5 |
| 55 | 50.0 |
| 56 | 50.6 |
| 57 | 51.1 |
| 58 | 51.7 |
| 59 | 52.2 |
| 60 | 52.8 |
| 61 | 53.3 |
| 62 | 53.9 |
| 63 | 54.4 |
| 64 | 55.0 |
| 65 | 55.6 |
| 66 | 56.1 |
| 67 | 56.7 |
| 68 | 57.2 |
| 69 | 57.8 |
| 70 | 58.3 |
| 71 | 58.9 |
| 72 | 59.4 |
| 73 | 60.0 |
| 74 | 60.5 |
| 75 | 61.1 |
| 76 | 61.7 |
| 77 | 62.2 |
| 78 | 62.8 |
| 79 | 63.3 |
| 80 | 63.9 |
| 81 | 64.4 |
| 82 | 65.0 |
| 83 | 65.5 |
| 84 | 66.1 |
| 85 | 66.6 |
| 86 | 67.2 |
| 87 | 67.8 |
| 88 | 68.3 |
| 89 | 68.9 |
| 90 | 69.4 |
| 91 | 70.0 |
| 92 | 70.5 |
| 93 | 71.1 |
| 94 | 71.6 |
| 95 | 72.2 |
| 96 | 72.7 |
| 97 | 73.3 |
| 98 | 73.9 |
| 99 | 74.4 |
| 100 | 75.0 |

The diesel fuel industry today continues to be burdened by the complex program of producing and validating T and U Secondary Fuel pair batches every one or two years for use in measurement of Cetane Numbers of diesel fuels and diesel components using the CFR engines and ASTM test method D613-10a.

As mentioned earlier, the low Cetane Number Primary Reference Standard, HMN of the 98% minimum purity level required is not currently available in large quantities. Also, the very small laboratory quantities that are available are cost prohibitive. The diesel fuels industry has therefore resorted to using Secondary Reference T and U Fuels. Ideally, the industry requires a substitute for HMN that can be produced in large quantities at reasonable cost so that the HMN substitute can be used not only to standardize the T and U Secondary Fuel blends, but the CFR engines of the ASTM D613 could be standardized to utilize blends of Primary Reference Fuels, n-cetane and a HMN replacement.

In addition to the CFR engine test as specified in ASTM D613, there are other alternatives to describe ignition quality. These tests include Cetane Index, which is calculated from other fuel properties such as density and volatility, and Derived Cetane Number (DCN) calculated from the ignition delay time measured using a constant volume combustion chamber method. Cetane Index is based on the fact that ignition quality is linked to hydrocarbon composition: n-paraffins have high ignition quality, and aromatic and naphthenic compounds have low ignition quality. Cetane Index being a calculated value, only provides an approximate indication of actual ignition quality.

The DCN is determined by measuring ignition delay in a constant chamber method. One method that has emerged is a combustion-based analytical method that was originally developed at Southwest Research Institute (ASTM D6890). It is referred to as the Constant Volume Combustion Apparatus (CVCA). A commercial apparatus utilizing this technique, introduced by Advanced Engine Technologies, is known as the Ignition Quality Tester (IQT). In this test, a small specimen of diesel fuel is injected into the heated, temperature controlled constant volume chamber which has previously been charged with compressed air. Ignition delay is measured using sensors that detect the start of fuel injection and the start of combustion for each cycle. Calibration of the apparatus is carried out with two reference materials: n-heptane and methylcyclohexane. The heptane is assigned an average ignition delay of 3.78±0.01 ms while the methylcyclohexane is assigned an ignition delay of 10.4±0.6 ms. The DCN is calculated using an equation that correlates a combustion ignition delay result to actual Cetane Number measured in the engine (ASTM D613).

Another test based on Ignition Delay to determine the DCN is ASTM D7170. The instrument to perform the DCN test here is offered by Waukesha and is known as the Fuel Ignition Tester (FIT). FIT also uses n-heptane and methylcyclohexane for calibration.

Yet another method for DCN is the Cetane ID (CID) 510 by PAC. This method is outlined in ASTM D7668 and uses the Ignition Delay measurement in a CVCA and correlates it to Cetane Number measured in an engine (ASTM D613).

An objective of certain aspects of this disclosure involves replacing mixtures of n-cetane and HMN as Primary Reference Fuels for calibration of the CFR engines (ASTM D613) and the calibration of the IQT (ASTM D6890), FIT (ASTM D7170) and CID (ASTM D7668) with mixtures of n-cetane and a lower cost, more easily available compound that HMN, but which has a Cetane Number that is nearly the same as that of HMN, and which produces blends having performance characteristics similar or substantially the same as HMN/n-cetane blends.

SUMMARY OF THE DISCLOSURE

Since HMN of required purity is not available in large quantities and is expensive, the industry is in need of another chemical that can be easily produced and can be a direct replacement for HMN. Disclosed herein is a chemical substance whose combustion properties under compression ignition were similar to HMN.

It has been found that, surprisingly, 2,2,4,6,6-pentamethylheptane (PMH) behaves very similar to HMN in a CFR engine as described in ASTM D613. Accordingly, this disclosure is directed to use of PMH and/or other isoparaffins having 12 carbon atoms as low-cost Primary Reference standard for determining Cetane Number and/or Derived Cetane Number, such as in any of the processes previously discussed which use HMN as a Primary Reference standard.

DETAILED DESCRIPTION

Figure 1:
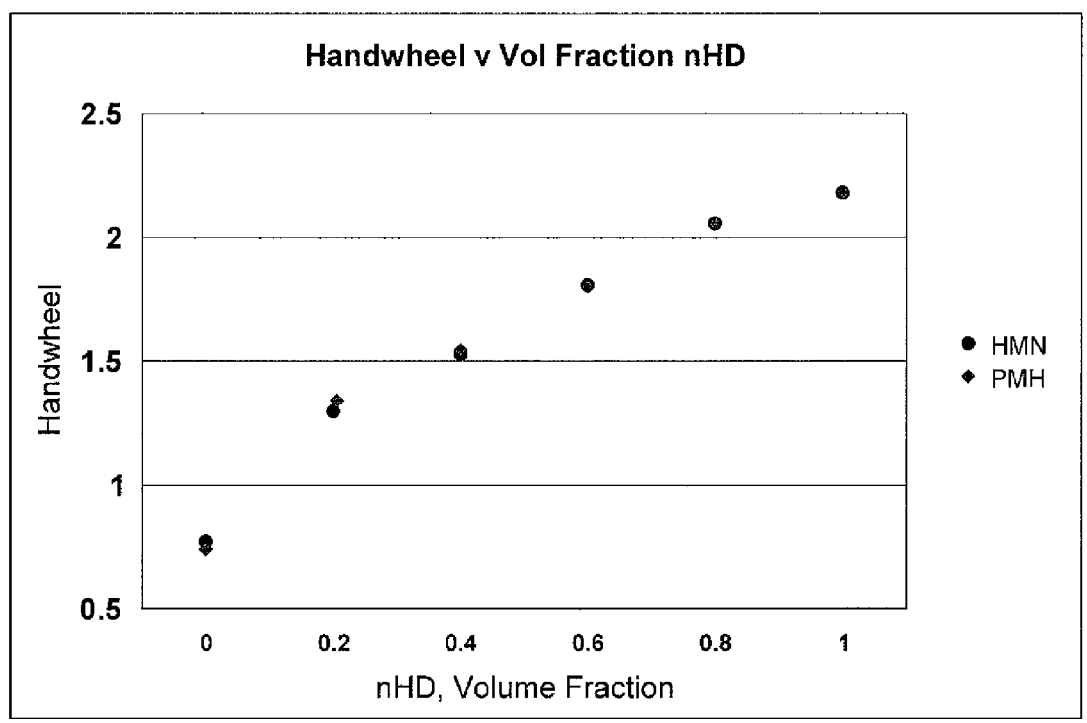
FIG. 1 is a graph comparing hand-wheel readings, an arbitrary numerical value related to compression ratio, obtained from a micrometer scale that indicates a position of a variable compression plug in a precombustion chamber of a test engine, for various blends of n-cetane and HMN to hand-wheel readings of blends of n-cetane and PMH using the same test equipment and conditions.

The compositions disclosed herein consist essentially of a blend of n-hexadecane and an isoparaffin having 12 carbon atoms or a mixture of isoparaffins having 12 carbon atoms. This means that the compositions do not include any materials, whether deliberately added or inadvertent impurities, that would substantially adversely affect the ability to use the compositions as standards for determining Cetane Number. Both the n-hexadecane and isoparaffin(s) having 12 carbon atoms should have a purity level that does not adversely affect their utility as a standard for evaluating Cetane Number. As indicated in ASTM D613-10a, the n-cetane (n-hexadecane) should have a minimum purity of 99% as determined by chromatographic analysis. In the case of the isoparaffin(s) having 12 carbon atoms, testing quality comparable to the established ASTM D613-10a standard using heptamethylnonane (2,2,4,4,6,8,8-heptamethylnonane) at a minimum purity of 98% as determined by chromatographic analysis can be achieved with a modified procedure substituting isoparaffin(s) having 12 carbon atoms for the heptamethylnonane used in ASTM D613-10a, wherein the purity of the isoparaffin(s) is a minimum of 98% or 99% by weight as determined by chromatographic analysis. It has been found that a process of oligomerizing isobutylene to produce triisobutylene, distilling the product to separate the C-12 components, and subsequently hydrogenating the purified triisobutylene, can be used to obtain 2,2,4,6,6-pentamethylheptane at purity levels in excess of 98% or 99% by weight. In these processes, impurities are limited to very small amounts of intermediates and by-products and small traces of other impurities such as water and sulfur (in the parts per million range) that do not adversely affect the ability to use the isoparaffins having 12 carbon atoms as a primary standard in a modified ASTM D613-10a test procedure for determining Cetane Number.

Test procedures, equipment, conditions, etc. in accordance with ASTM D613-10a were used to compare the combustion characteristics of various blends of n-cetane (nHD) and HMN to blends of n-cetane and PMH. In these tests, an operator of a CFR engine uses a hand-wheel to increase the compression ratio (and therefore the peak pressure within the cylinder) of the engine until the time between fuel injection and ignition is 2.407 ms. The resulting Cetane Number is then calculated by determining which mixture of nHD and HMN will result in the same ignition delay. The compositions of the blends are shown in Table 1. The results from the performance of various mixtures of nHD-HMN and nHD-PMH are shown in Table 2.

TABLE 1

| Blend | Volume Fraction | | | calc. CN |
|---|---|---|---|---|
| | HMN | PMH | nHD | |
| 1 | | | 1 | 100.0 |
| 2 | 0.2 | | 0.8 | 83.0 |
| 3 | | 0.2 | 0.8 | |
| 4 | | 0.4 | 0.6 | |
| 5 | 0.4 | | 0.6 | 66.0 |

TABLE 1-continued

| Blend | Volume Fraction | | | |
|---|---|---|---|---|
| | HMN | PMH | nHD | |
| 6 | 0.6 | | 0.4 | 49.0 |
| 7 | | 0.6 | 0.4 | |
| 8 | | 0.8 | 0.2 | |
| 9 | 0.8 | | 0.2 | 32.0 |
| 10 | 1 | | | 15.0 |
| 11 | | 1 | | |

| | HMN | PMH | nHD | 1-Methylnaphthalene |
|---|---|---|---|---|
| Density (measured at 15.56° C.) | 0.7874 | 0.7484 | 0.7779 | 1.001 |
| Molecular Wt. | 226.44 | 170.33 | 226.44 | 142.2 |
| Boiling Point (° C.) | 240 | 180 | 287 | 242 |
| Blend size, mL | 750 | | | |

TABLE 2

Comparison of PMH to HMN in Blends with nHD.
Hand-Wheel and Micrometer Readings for Program Samples

| | Blend 1 | T-25 | Blend 1 | T-25 | Blend 1 | T-25 | Averages |
|---|---|---|---|---|---|---|---|
| Blend 1 Handwheel | 2.153 | | 2.194 | | 2.194 | | 2.180333 |
| T-25 Handwheel | | 1.934 | | 1.96 | | 1.96 | 1.951333 |
| Blend 1 Inj Adv Mic Setting | 831 | | 850 | | 850 | | 843.667 |
| T-25 Inj Adv Mic Setting | | 853 | | 855 | | 855 | 854.333 |
| Fuel Mic Setting | 680 | 670 | | | | | |

| | Blend 2 | Blend 3 | Blend 2 | Blend 3 | Blend 2 | Blend 3 | Averages |
|---|---|---|---|---|---|---|---|
| Blend 2 Handwheel | 2.024 | | 2.073 | | 2.073 | | 2.057 |
| Blend 3 Handwheel | | 2.032 | | 2.068 | | 2.068 | 2.056 |
| Blend 2 Inj Adv Mic Setting | 855 | | 850 | | 850 | | 851.667 |
| Blend 3 Inj Adv Mic Setting | | 844 | | 840 | | 840 | 841.333 |
| Fuel Mic Setting | 675 | 675 | | | | | |

| | Blend 4 | Blend 5 | Blend 4 | Blend 5 | Blend 4 | Blend 5 | Averages |
|---|---|---|---|---|---|---|---|
| Blend 4 Handwheel | 1.815 | | 1.8 | | 1.792 | | 1.802 |
| Blend 5 Handwheel | | 1.808 | | 1.808 | | 1.808 | 1.808 |
| Blend 4 Inj Adv Mic Setting | 852 | | 846 | | 846 | | 848.000 |
| Blend 5 Inj Adv Mic Setting | | 872 | | 865 | | 865 | 867.333 |
| Fuel Mic Setting | 670 | 670 | | | | | |

| | Blend 6 | Blend 7 | Blend 6 | Blend 7 | Blend 6 | Blend 7 | Averages |
|---|---|---|---|---|---|---|---|
| Blend 6 Handwheel | 1.519 | | 1.534 | | 1.527 | | 1.527 |
| Blend 7 Handwheel | | 1.548 | | 1.537 | | 1.55 | 1.545 |
| Blend 6 Inj Adv Mic Setting | 859 | | 854 | | 861 | | 858.000 |
| Blend 7 Inj Adv Mic Setting | | 852 | | 833 | | 838 | 841.000 |
| Fuel Mic Setting | 670 | 665 | | | | | |

| | Blend 8 | Blend 9 | Blend 8 | Blend 9 | Blend 8 | Blend 9 | Averages |
|---|---|---|---|---|---|---|---|
| Blend 8 Handwheel | 1.339 | | 1.342 | | 1.342 | | 1.341 |
| Blend 9 Handwheel | | 1.305 | | 1.295 | | 1.29 | 1.297 |
| Blend 8 Inj Adv Mic Setting | 859 | | 859 | | 859 | | 859.000 |
| Blend 9 Inj Adv Mic Setting | | 846 | | 846 | | 836 | 842.667 |
| Fuel Mic Setting | 665 | 675 | | | | | |

| | Blend 10 | Blend 11 | Blend 10 | Blend 11 | Blend 10 | Blend 11 | Averages |
|---|---|---|---|---|---|---|---|
| Blend 10 Handwheel | 0.767 | | 0.782 | | 0.7655 | | 0.772 |
| Blend 11 Handwheel | | 0.741 | | 0.743 | | 0.738 | 0.741 |
| Blend 10 Inj Adv Mic Setting | 680 | | 644 | | 643 | | 655.667 |
| Blend 11 Inj Adv Mic Setting | | 698 | | 712 | | 662 | 690.667 |
| Fuel Mic Setting | 670 | 670 | | | | | |

As indicated in FIG. 1, the combustion characteristics of PMH and HMN are essentially the same. Surprisingly, it was found that the performance of the HMN, a C-16 isoparaffin and PMH, a C-12 iso-paraffin, are almost identical. Thus, Cetane Number can be accurately determined using a modified version of the ASTM-D613-10a standard in which PMH is used as a direct substitute for HMN.

Figure 2:
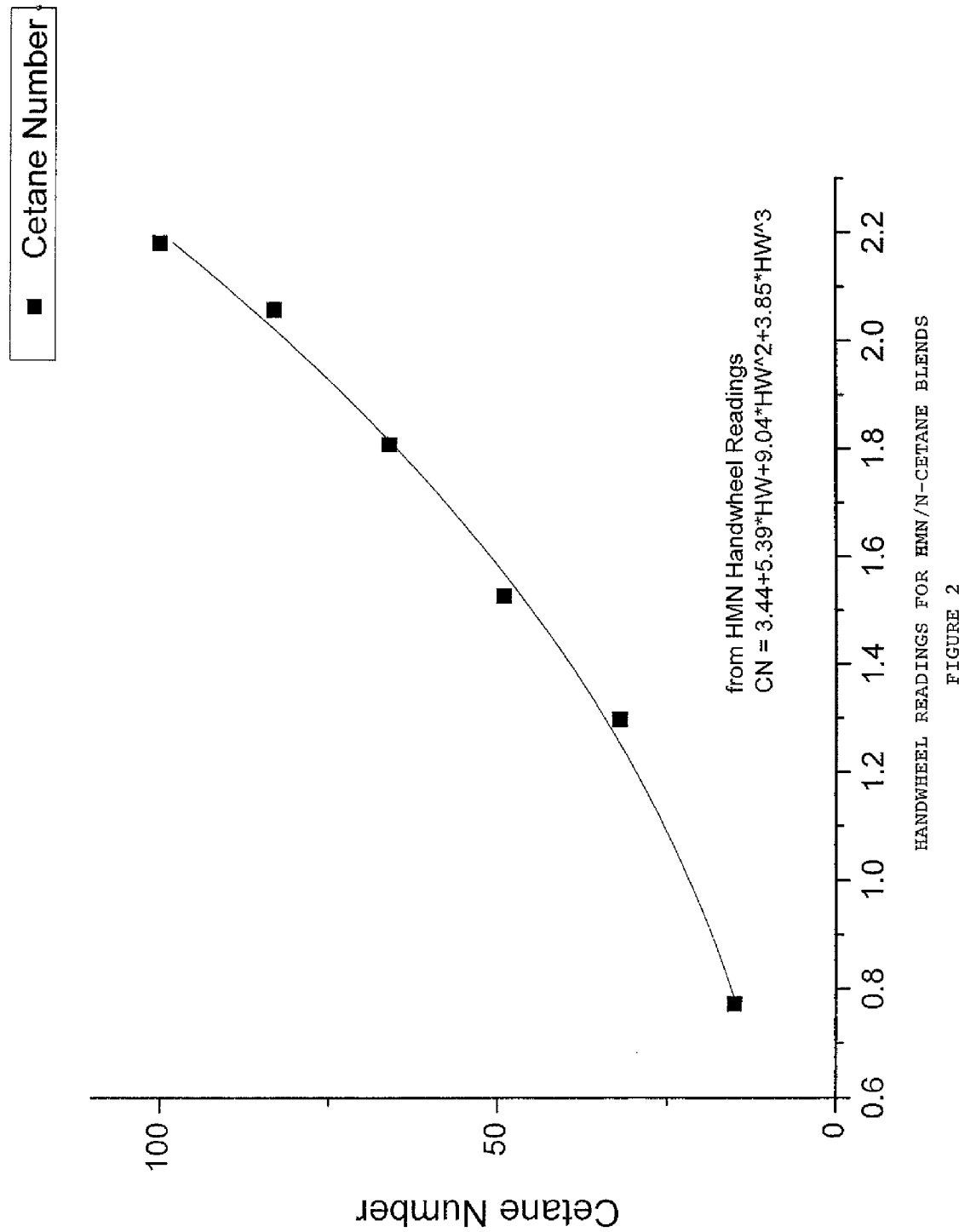
FIG. 2 is a graph of Cetane Number versus hand-wheel readings for blends of n-cetane and 2,2,4,4,6,8,8-heptamethylnonane (HMN) for the test engine and apparatus used throughout this disclosure.

A graph correlating handwheel measurement to Cetane Number in accordance with the procedures of ASTM D613-10a for the engine used for generating the data in Table 2 is shown in FIG. 2. A least squares method shows that the data can be accurately represented by the curve shown in FIG. 2, which is a graphical representation of the equation CN=3.44+ 5.39 (HW)+9.04 (HW)$^2$+3.85 (HW)$^3$, wherein CN is Cetane Number and HW is the Handwheel measurement.

TABLE 3 from Origin: CN = 3.44165 + 5.38817 * HW + 9.04211 * HW^2 + 3.84683 * HW^3

| n-cetane | HMN | PMH | HW | Assigned Cetane Number | Experimentally Determined Cetane Number for HMN/n-cetane Blends | Experimentally Determined Cetane Number for PMH/n-cetane Blends |
|---|---|---|---|---|---|---|
| 100% | 0 | 0 | 2.180 | 100.0 | 98.0 | 98.0 |
| 80% | 20% | — | 2.057 | 83.0 | 86.3 | |
| 80% | — | 20% | 2.056 | | | 86.2 |
| 60% | 40% | — | 1.802 | | | 65.0 |
| 60% | — | 40% | 1.808 | 66.0 | 65.5 | |
| 40% | 60% | — | 1.527 | 49.0 | 46.4 | |
| 40% | — | 60% | 1.545 | | | 47.5 |
| 20% | 80% | — | 1.341 | | | 36.2 |
| 20% | — | 80% | 1.297 | 32.0 | 34.0 | |
| 0% | 100% | — | 0.772 | 15.0 | 14.8 | |
| 0% | — | 100% | 0.741 | | | 14.0 |

Table 3 shows the assigned or theoretical Cetane Number associated with the measured handwheel readings for the various blends in Table 1 compared with the experimentally determined Cetane Number based on correlating measured handwheel readings to Cetane Number using the equation developed from the data in FIG. 2. The data indicate, among other things, that the experimentally determined Cetane Number for PMH is about 14.0. By repeating the experiments with different engines at different laboratory facilities, it will be possible to develop agreement in the industry as to the appropriate Cetane Number or Accepted Reference Value (ARV) to assign to PMH. This would allow PMH to be used as a primary standard in the various accepted standards for determining Cetane Number or a Derived Cetane Number replacing the expensive HMN primary standard with inexpensive PMH and replacing the assigned Cetane Number for HMN (i.e., 15) with an Accepted Reference Value for the Cetane Number of PMH.

This means that PMH can directly replace HMN as a Primary Standard for the measurement of Cetane Number (CN), Derived Cetane Number (DCN) and ignition delay of diesel fuels and diesel fuel blending components. Since PMH can be produced in large quantities and at reasonable cost compared to HMN, PMH can eliminate the need to use the Secondary T and U fuels currently used for standardizing diesel fuel combustion characteristics. The process of producing Secondary T and U fuels is complicated and involves the use of difficult to procure HMN to calibrate the T and U fuels.

The advantage of using PMH instead of HMN is that PMH can be used directly as a Primary Standard for the measurement of Cetane Number (CN), Derived Cetane Number (DCN) and ignition delay of diesel fuels and diesel fuel blending components. There will be no need to produce Secondary Reference T and U fuel pairs.

The disclosed reference standards can be used directly as substitutes for blends of n-hexadecane and 2,2,4,4,6,8,8-heptamethylnonane in ASTM D613-10a for determining Cetane Number, or in ASTM D6890, ASTM D7170 or ASTM D7668 to determine a Derived Cetane Number.

What is claimed is:

1. A composition useful as a reference standard for measurement of a Cetane Number of a fuel, consisting of a blend of (1) n-hexadecane and (2) 2,2,4,6,6-pentamethylheptane, wherein the 2,2,4,6,6-pentamethylheptane has a minimum purity of at least 98% and the n-hexadecane has a minimum purity of at least 99%, such that the total amount of n-hexadecane and 2,2,4,6,6-pentamethylheptane in the blend is greater than 98%.

2. A process for determining the Cetane Number of a test sample, comprising:
    comparing the combustion characteristics of the test sample in a test engine with the combustion characteristics of a reference fuel consisting essentially of (1) a blend of n-hexadecane and (2) 2,2,4,6,6-pentamethylheptane, wherein the 2,2,4,6,6-pentamethylheptane has a minimum purity of at least 98% such that the total amount of n-hexadecane and 2,2,4,6,6-pentamethylheptane in the blend is greater than 98%; and
    determining a Cetane Number of the test sample based on the comparison.

3. The process of claim 2, wherein the isoparaffin having 12 carbon atoms or a combination of isoparaffins has a purity level of at least 98% by weight as determined by chromatographic analysis.

4. The process of claim 2, wherein the isoparaffin having 12 carbon atoms or a combination of isoparaffins has a purity level of at least 99% by weight as determined by chromatographic analysis.

5. The process of claim 2, wherein the isoparaffin having 12 carbon atoms or a combination of isoparaffins comprises at least 98% by weight 2,2,4,6,6-pentamethylheptane.

6. The process of claim 2, wherein the isoparaffin having 12 carbon atoms or a combination of isoparaffins comprises at least 99% by weight 2,2,4,6,6-pentamethylheptane.

7. A process for determining a derived Cetane Number in accordance with ASTM D6890, ASTM D7170 or ASTM D7668 using a measurement characteristic of Ignition Delay and an equation correlating the measured characteristic of Ignition Delay to the measured Ignition Delay of a Reference Standard consisting essentially of (1) a blend of n-hexadecane and (2) 2,2,4,6,6-pentamethylheptane, wherein the 2,2,4,6,6-pentamethylheptane has a minimum purity of at least 98% such that the total amount of n-hexadecane and 2,2,4,6,6-pentamethylheptane in the blend is greater than 98%.

8. The process of claim 7, wherein the isoparaffin having 12 carbon atoms is 2,2,4,6,6-pentamethylheptane having a purity level of at least 98% by weight.

9. The process of claim 7, wherein the isoparaffin having 12 carbon atoms is 2,2,4,6,6-pentamethylheptane having a purity level of at least 99% by weight.

* * * * *